United States Patent [19]
Barber

[11] Patent Number: 5,236,460
[45] Date of Patent: Aug. 17, 1993

[54] VERTEBRAL BODY PROSTHESIS

[75] Inventor: Forest C. Barber, Fort Worth, Tex.

[73] Assignee: Midas Rex Pneumatic Tools, Inc., Fort Worth, Tex.

[21] Appl. No.: 774,208

[22] Filed: Oct. 10, 1991

Related U.S. Application Data

[63] Continuation-in-part of Ser. No. 425,464, Feb. 12, 1990.

[51] Int. Cl.⁵ .................................................. A61F 2/44
[52] U.S. Cl. ........................................ 623/17; 623/26; 606/61; 403/31; 403/109; 403/5
[58] Field of Search ............... 623/17, 16, 26; 606/61, 606/63; 403/5, 31, 37, 109, 377, 378

[56] References Cited

U.S. PATENT DOCUMENTS

| | | | |
|---|---|---|---|
| 2,465,677 | 3/1949 | Deverall | 403/31 X |
| 2,714,331 | 8/1955 | Plante | 403/109 X |
| 4,157,715 | 6/1979 | Westerhoff | 606/63 X |
| 4,599,086 | 7/1986 | Doty | 623/17 |
| 4,932,969 | 6/1990 | Frey et al. | 623/17 |
| 4,932,975 | 6/1990 | Main et al. | 623/17 |
| 4,946,378 | 8/1990 | Hirayama et al. | 623/17 |
| 5,002,576 | 3/1991 | Fuhrmann et al. | 623/17 |

FOREIGN PATENT DOCUMENTS

| | | | |
|---|---|---|---|
| 3729600 | 3/1989 | Fed. Rep. of Germany | 623/17 |
| 0137414 | 6/1987 | Japan | 403/37 |
| 1124955 | 11/1984 | U.S.S.R. | 606/61 |
| 1560184 | 4/1990 | U.S.S.R. | 623/17 |
| 2219060 | 11/1989 | United Kingdom | 403/109 |

Primary Examiner—Randall L. Green
Assistant Examiner—O. Willse
Attorney, Agent, or Firm—James E. Bradley

[57] ABSTRACT

A vertebral prosthesis locates between vertebral bodies of a human body. The prosthesis has tubular inner and outer bodies that telescope relative to each other. Each body has a platform on its end. The platform secures to adjacent vertebral bodies. Sharp pins on the platform pierce the vertebral bodies to stabilize the prosthesis. A bracket slides laterally and secures by screws to sides of the vertebral bodies.

11 Claims, 3 Drawing Sheets

5,236,460

VERTEBRAL BODY PROSTHESIS

CROSS REFERENCE TO RELATED APPLICATION

This application is a continuation-in-part of application Ser. No. 07/425,464, filed Feb. 12, 1990, Forest C. Barber.

BACKGROUND OF THE INVENTION

1. Field of the invention:

This invention relates in general to a prosthesis implant for vertebra, and in particular to a prosthesis that is extensible in length.

2. Description of the Prior Art:

There are occasions when a vertebral body, which is a portion of the spine, must be removed because of disease, damage, or congenital deformation. In such case, a prosthesis can be inserted in place of the vertebral body that has been removed. Various types have been used in the past. However, there are shortcomings, such as difficulty in installing and securing the prosthesis in place.

SUMMARY OF THE INVENTION

The prosthesis of this invention is a telescoping or expansible member. It has an outer body that is tubular and has an axial bore. An inner body is carried in the outer body. The outer body has a port through which a liquid may be introduced to cause the bodies to move apart and lengthen the assembly. The liquid may be either an incompressible hydraulic liquid, or it may be a hardenable resin.

Platforms are located on the upper and lower ends of the assemblies. Each platform has a plurality of pins that pierce soft portions of the vertebral body to secure the assembly in place. Preferably one of the pins is secured to a piston located within the inner body. The liquid not only causes the inner and outer bodies to telescope, but it also causes the piston to move relative to the bodies to cause the pin to drive into the bone.

The securing means also includes a bracket that mounts slidably to each of the platforms. The bracket has a vertically extending flange for receiving a screw to secure the flange to a vertebral body.

DETAILED DESCRIPTION OF THE INVENTION

Figure 1:
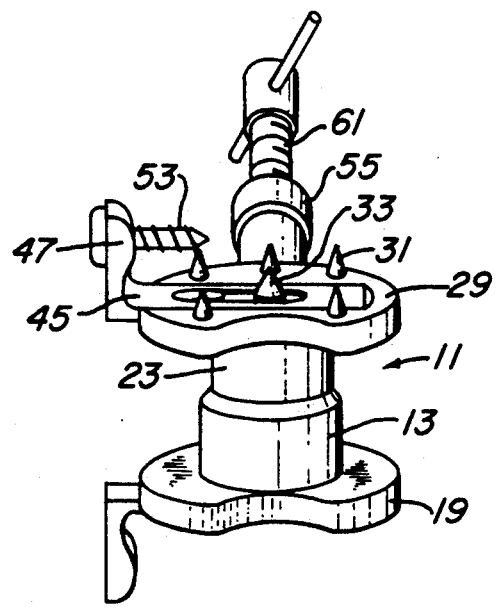
FIG. 1 is a perspective view showing a first embodiment of a prosthesis constructed in accordance with this invention, and showing also an installation tool secured to the prosthesis.
Figure 2:
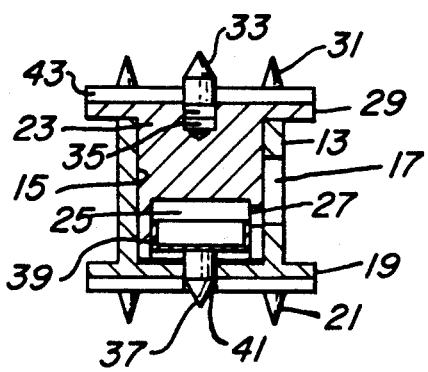
FIG. 2 is a vertical sectional view of the prosthesis of FIG. 1, showing the inner and outer bodies in a contracted position.
Figure 3:
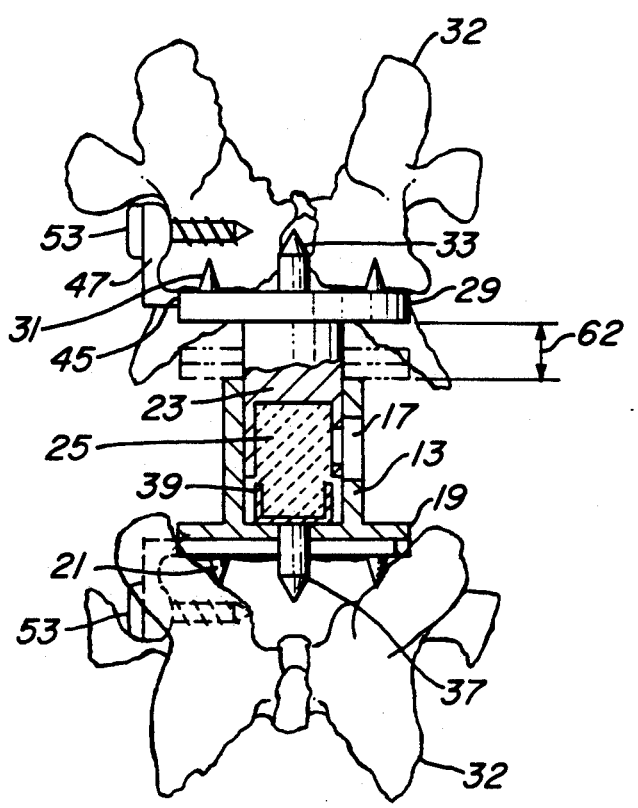
FIG. 3 is a sectional view of the prosthesis of FIG. 1, showing the inner and outer bodies in an extended position and secured to adjacent vertebral bodies.

Referring to FIGS. 1, 2 and 3, prosthesis 11 has an outer tubular body 13. Outer body 13 has an axial bore 15. A port 17 extends through the sidewall of outer body 13. A lower flange or platform 19 is located on the lower end of outer body 13. Platform 19 has a greater diameter than the tubular portion of outer body 13. A plurality of pins 21, each having a sharp tip, protrude downward from lower platform 19.

Prosthesis 11 also has an inner body 23 which telescopingly mounts to the outer body 13. Inner body 23 has a lower tubular portion defining a cavity 25. Inner body 23 will slide axially within bore 15 from the retracted position shown in FIG. 2 to the extended position shown in FIG. 3. Seals (not shown) prevent leakage of any fluid. Inner body 23 has a port 27 through its side wall to admit liquid from port 17 to cavity 25.

Inner body 23 has an upper platform 29 that has the same diameter and is parallel to lower platform 19. Upper platform 29 has a plurality of sharp pins 31 that extend upward. As shown in FIG. 3, when the prosthesis 11 moves to the extended position, the pins 21, 31 will pierce soft portions of the spinal bone or vertebral bodies 32.

An axial pin 33 is secured by threads 35 to upper platform 29. Axial pin 33 is located on the axis of inner body 23. Axial pin 33 has a sharp tip and normally will protrude a greater distance than the pins 31.

A lower axial pin 37 mounts to a piston 39 carried in the cavity 25. Piston 39 moves from an upper position shown in FIG. 2 to a lower position shown in FIG. 3 when liquid is introduced through the ports 17, 27. Pin 37 protrudes through an axial hole 41 located in lower platform 19. Pin 37 will protrude a greater distance than the pins 21. Pin 37 will also pierce and anchor in soft portions of one of the vertebral bodies 32.

Figure 4:
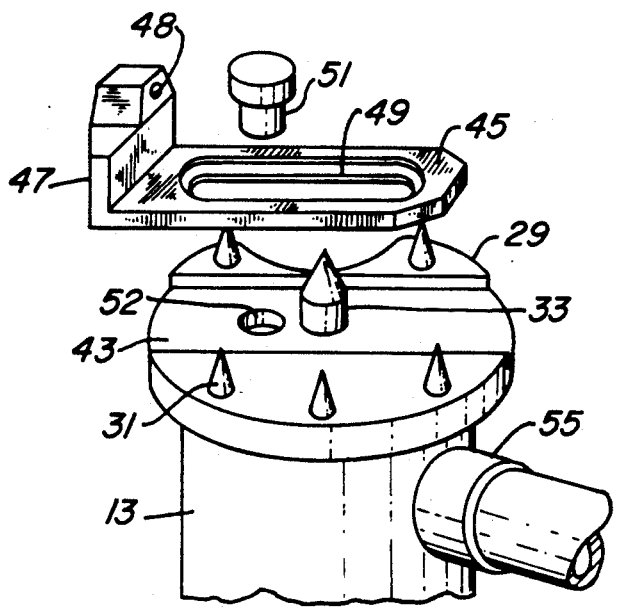
FIG. 4 is a partial, exploded perspective view of the prosthesis of FIG. 1, as seen from the upper side.

Referring to FIG. 4, the securing means for securing the prosthesis to vertebral bodies 32 includes not only the various pins 21, 31, 33 and 37, but also a bracket 45. Bracket 45 is a flat plate that mounts to each of the platforms 19, 29. Bracket 45 locates within a slot 43 formed in the platform 29. Slot 43 is a generally rectangular slot extending across the center of platform 29. Bracket 45 has a flange 47 located on one side that extends 90 degrees relative to the remaining portions of bracket 45. Flange 47 extends upward and has a hole 48 for receiving a screw 53 (FIG. 3). Screw 53 will secure within a hole drilled in each vertebral body 32.

Bracket 45 has an elongated slot 49 that accommodates the axial pin 33, and allows lateral sliding movement of bracket 45 to a desired position. A locking pin 51 also locates in slot 49 and secures within a hole 52 formed in the platform 29. Pin 51 will retain the bracket 45 but allow it to slide laterally relative to the axis of the prosthesis 11.

Figure 5:
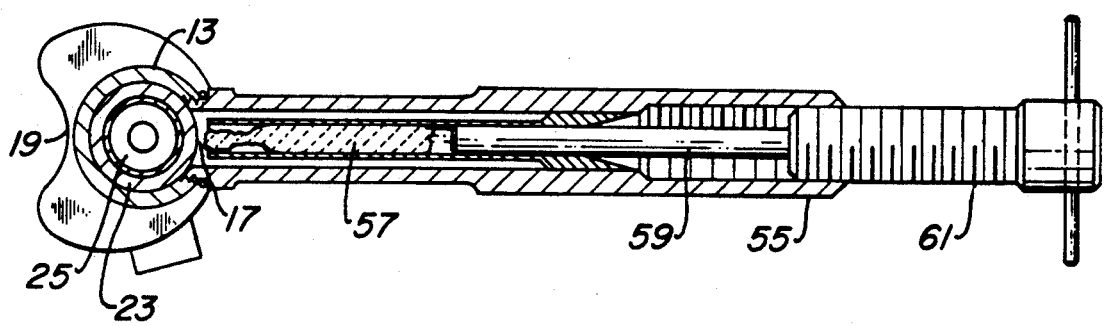
FIG. 5 is a horizontal sectional view of the prosthesis and installation tool of FIG. 1.
Figure 6:
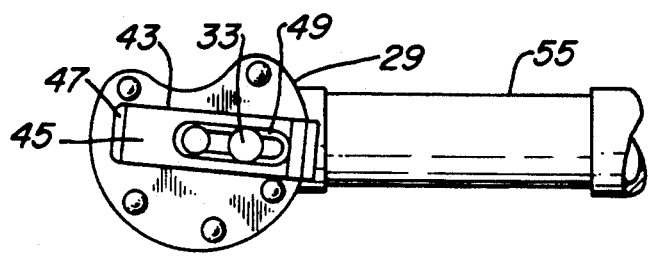
FIG. 6 is a top view of a portion of the prosthesis and installation tool of FIG. 1.

FIGS. 5 and 6 illustrate an installation tool for injecting a liquid into the prosthesis 11. The installation tool 55 will secure by threads to the port 17 in the outer body 13. Installation tool 55 in the embodiment of FIG.

5 is used to inject a resin packet 57. The resin packet 57 contains a liquid resin that once injected into the prosthesis 11, will harden to a rigid mass. A plunger 59 will push the resin of resin packet 57 through a hole in the injecting tool 55. Plunger 59 is moved forward by means of a threaded handle 61.

In operation, referring to FIGS. 1-6, the surgeon would remove the diseased vertebral body 32. The surgeon places a resin packet 57 in tool 55. The surgeon secures tool 55 to prosthesis 11 by securing tool 55 to threads in the outer body port 17. The user then inserts the prosthesis 11 between the two vertebral bodies 32, utilizing the tool 55 to hold the prosthesis 11 in place. The surgeon then will rotate handle 61. This causes resin packet 57 to rupture.

Plunger 59 will push the resin through the outer body port 17, through the inner body port 27 and into the cavity 25. The fluid will cause the inner body 23 and outer body 13 to move apart from each other. Also, the pressure of the resin 57 will push the piston 39 downward. This causes the pin 37 to pierce soft tissue of the vertebral body 32. Further rotation of handle 61 causes the inner body 23 and outer body 13 to move farther apart from each other until the desired length has been achieved as shown in FIG. 3. The dotted lines indicate the original position, with the solid lines the final position. The increase in length is indicated by the dimension 62.

The surgeon will allow the resin 57 time to cure into a hardened mass. The surgeon will then unscrew the tool 55 from the outer body 13. Hardened portions of the resin in outer body port 17 may be broken off. A plug (not shown) may then be screwed into outer body port 17 to close the outer body port 17. The surgeon drills a hole in vertebral body 32 and inserts a screw 53 through the bracket flange 47.

Figure 7:
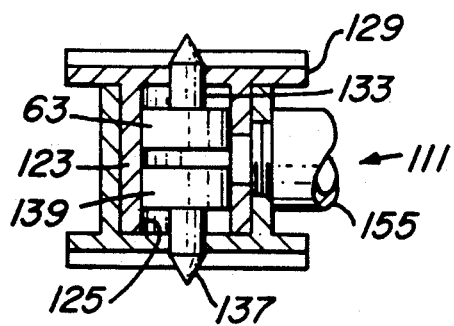
FIG. 7 is a sectional view of a second embodiment of the prosthesis of FIG. 1.

FIG. 7 shows a second embodiment of the prosthesis 11. In this embodiment, a second piston 63 locates in cavity 125 of inner body 123. Axial pin 133 is secured to piston 63 for movement therewith. Axial pin 133 extends through a hole in the upper platform 129. Liquid introduced by the tool 155 causes the pistons 63, 139 to move in opposite directions. This drives the pins 133, 137 in opposite directions to secure the prosthesis 111.

Figure 8:
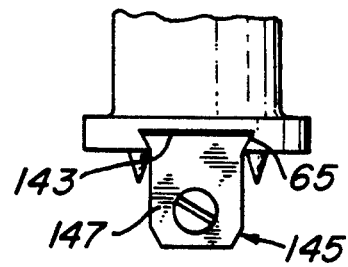
FIG. 8 is a third embodiment of the prosthesis of FIG. 1.

FIG. 8 illustrates another alternate embodiment to the prosthesis 11 of FIG. 1. In this embodiment, the bracket 145 and flange 147 are retained by a dovetail shoulder 65. The dovetail shoulder 65 is formed in the slot 143. This arrangement may be used to retain the bracket 145 rather than the pin 51 illustrated in FIG. 4.

Figure 9:
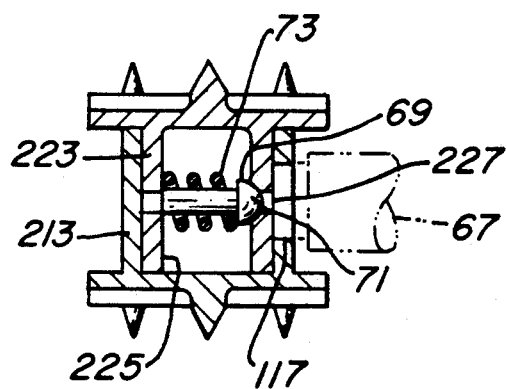
FIG. 9 is a fourth embodiment of the prosthesis of FIG. 1.

FIG. 9 illustrates another alternate embodiment to the prosthesis 11 in FIG. 1. In this embodiment, the prosthesis utilizes a liquid that does not set into a rigid mass. This liquid will be a hydraulic, incompressible fluid introduced by a pump 67. A check valve 69 will allow the liquid to be introduced into cavity 225 of inner body 223. Check valve 69 prevents liquid from flowing out. Check valve 69 may be of various types, such as one utilizing a plunger 71 and spring 73. Plunger 71 acts against the inner body port 227. The trapped liquid will retain the outer body 213 and inner body 223 in an extended position.

Figure 10:
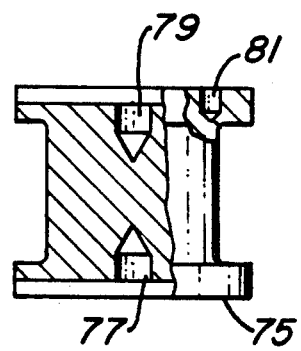
FIG. 10 shows an extension block used to be stacked between two of the prosthesis of FIG. 1.
Figure 11:
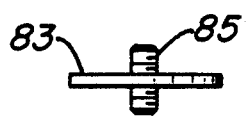
FIG. 11 shows a screw plate for use with the prosthesis of FIG. 1 to stack more than one of the prosthesis together.

FIG. 10 shows an extension member 75 that may be mounted between two of the prosthesis 11 as shown in FIG. 11, to stack them together for greater length. This would be utilized in a case of a number of vertebral bodies 32 being removed. Extension member 75 is a cylindrical member fixed in length. It has a lower recess 77 which receives an upper axial pin 33 (FIG. 3) of a prosthesis 11. It has a platform 75 that mates with a lower platform 19 of a prosthesis 11. Extension member 75 has recesses 79, 81 on its upper end for receiving pins 37 and 21 of a prostheses 11.

FIG. 11 illustrates a screw plate 83 which may be used to secure two of the prosthesis 11 together in a stacked relationship. Screw plate 83 has threads 85. The threads 85 would engage the threads 35 in the prosthesis 11 as shown in FIG. 2.

The invention has significant advantages. The prosthesis is easily and quickly installable in place of a resected vertebral body. The telescoping inner and outer bodies allow precise lengths to be achieved. The pointed tips of the pins firmly anchor the prosthesis in place. The sliding brackets provide additional stability. The devices can be stacked on one another and extended in length with an extension member.

While the invention has been shown in only a few of its forms, it should be apparent to those skilled in the art that it is not so limited, but is susceptible to various changes without departing from the scope of the invention.

I claim:

1. A vertebral prosthesis for positioning between vertebral bodies, comprising in combination:
   a tubular outer body having a platform on one end, a longitudinal axis and an axial bore;
   an inner body having a cylindrical portion carried in the bore of the outer body for sliding telescoping movement along the axis of the outer body, the inner body having a platform on one end that is located exterior of the outer body;
   securing means on each of the platforms for securing the platforms to adjacent vertebral bodies;
   port means for introducing a liquid into the bore of the outer body to cause the inner body to move axially relative to the outer body to provide a desired length for the prosthesis between platforms; and wherein each of the securing means comprises:
   a plurality of pins, each protruding in an axial direction from one of the platforms for anchoring in holes in one of the vertebral bodies;
   a bracket having a base and a flange which extends from one side of the bracket transverse to the base;
   means for mounting the base of the bracket to one of the platforms for sliding movement transverse to the axis of the outer body to position the flange at a selected lateral distance from the axis of the outer body; and
   fastener means for fastening the flange to one of the vertebral bodies.

2. A vertebral prosthesis for positioning between vertebral bodies, comprising in combination:
   a tubular outer body having a platform on one end, a longitudinal axis and an axial bore;
   an inner body having a cylindrical portion carried in the bore of the outer body for sliding telescoping movement along the axis of the outer body, the inner body having a platform on one end that is located exterior of the outer body;
   securing means on each of the platforms for securing the platforms to adjacent vertebral bodies;
   port means for introducing a liquid into the bore of the outer body to cause the inner body to move axially relative to the outer body to provide a desired length for the prosthesis between platforms; and wherein each of the securing means comprises:

a plurality of pins, each having a sharp tip, each protruding in an axial direction from one of the platforms for piercing and anchoring in soft portions of the vertebral bodies;

a bracket having a base and a flange which extends from one side of the bracket transverse to the base;

means for mounting the base of the bracket to one of the platforms for sliding movement transverse to the axis of the outer body to position the flange at a selected lateral distance from the axis of the outer body; and fastener means for fastening the flange to one of the vertebral bodies.

3. A vertebral prosthesis for positioning between vertebral bodies, comprising in combination:

a tubular outer body having a platform on one end, a longitudinal axis and an axial bore;

an inner body having a cylindrical portion carried in the bore of the outer body for sliding telescoping movement along the axis of the outer body, the inner body having a platform on one end that is located exterior of the outer body;

securing means on each of the platforms for securing the platforms to adjacent vertebral bodies;

port means for introducing a liquid into the bore of the outer body to cause the inner body to move axially relative to the outer body to provide a desired length for the prosthesis between platforms; and wherein at least one of the securing means comprises:

a pin having a sharp tip protruding in an axial direction through a hole provided in one of the platforms; and a piston carried in the outer body for relative movement thereto, the pin being mounted to the piston for movement therewith, the liquid being introduced into the outer body causing the piston to move to cause the pin to pierce and anchor in soft portions of one of the vertebral bodies.

4. A vertebral prosthesis for positioning between vertebral bodies, comprising in combination:

a tubular outer body having a platform on one end, a longitudinal axis and an axial bore;

an inner body having a cylindrical portion carried in the bore of the outer body for sliding telescoping movement along the axis of the outer body, the inner body having a platform on one end that is located exterior of the outer body;

securing means on each of the platforms for securing the platforms to adjacent vertebral bodies;

port means for introducing a liquid into the bore of the outer body to cause the inner body to move axially relative to the outer body to provide a desired length for the prosthesis between platforms; and wherein each of the securing means comprises:

a pin having a sharp time protruding in an axial direction through a hole provided in each of the platforms; and a piston carried in the outer body for relative movement thereto, the pin being mounted to the piston for movement therewith, the liquid being introduced into the outer body causing the piston to move axially to cause the pin to pierce and anchor in soft portions of the vertebral bodies.

5. A vertebral prosthesis for positioning between vertebral bodies, comprising in combination:

a tubular outer body having a platform on one end, a longitudinal axis and an axial bore;

an inner body having a cylindrical portion carried in the bore of the outer body for sliding telescoping movement along the axis of the outer body, the inner body having a platform on one end that is located exterior of the outer body;

securing means on each of the platforms for securing the platforms to adjacent vertebral bodies;

port means for introducing a liquid into the bore of the outer body to cause the inner body to move axially relative to the outer body to provide a desired length for the prosthesis between platforms; and wherein at least one of the securing means comprises:

a pin having a sharp tip protruding in an axial direction through a hole provided in one of the platforms;

a piston carried it the outer body for relative movement thereto, the pin being mounted to the piston for movement therewith, the liquid being introduced into the outer body causing the piston to move to cause the pin to pierce and anchor in soft portions of one of the vertebral bodies;

a bracket having a base and a flange which extends from one side of the bracket transverse to the base;

means for mounting the base of the bracket to one of the platforms for sliding movement transverse to the axis of the outer body to position the flange at a selected lateral distance from the axis of the outer body; and fastener means for fastening the flange to one of the vertebral bodies.

6. A vertebral prosthesis for positioning between vertebral bodies, comprising in combination:

a tubular outer body having a platform on one end, a longitudinal axis and an axial bore;

a tubular inner body having a cylindrical portion carried in the bore of the outer body for sliding telescoping movement along the axis of the outer body, the inner body having a platform on one end that is located exterior of the outer body;

securing means on each of the platforms for securing the platforms to adjacent vertebral bodies;

port means for introducing a liquid into the bore of the outer body to cause the inner body to move axially relative to the outer body to provide a desired length for the prosthesis between platforms, the liquid being of a type which cures to a rigid mass to retain the desired length; and wherein each of the securing means comprises:

a plurality of pins, each protruding in an axial direction from one of the platforms for anchoring in holes in one of the vertebral bodies;

a bracket having a base and a flange which extends from one side of the bracket transverse to the base;

means for mounting the base of the bracket to one of the platforms for sliding movement transverse to the axis of the outer body to position the flange at a selected lateral distance from the axis of the outer body; and fastener means for fastening the flange to one of the vertebral bodies.

7. A vertebral prosthesis for positioning between vertebral bodies, comprising in combination:

a tubular outer body having a platform on one end, a longitudinal axis and an axial bore;

a tubular inner body having a cylindrical portion carried in the bore of the outer body for sliding telescoping movement along the axis of the outer body, the inner body having a platform on one end that is located exterior of the outer body;

securing means on each of the platforms for securing the platforms to adjacent vertebral bodies;

port means for introducing a liquid into the bore of the outer body to cause the inner body to move axially relative to the outer body to provide a desired length for the prosthesis between platforms, the liquid being of a type which cures to a rigid mass to retain the desired length; and wherein each of the securing means comprises:

a plurality of pins, each having a sharp tip, each protruding in an axial direction from one of the platforms for piercing and anchoring in soft portions of the vertebral bodies;

a bracket having a base and a flange which extends from one side of the bracket transverse to the base;

means for mounting the base of the bracket to one of the platforms for sliding movement transverse to the axis of the outer body to position the flange at a selected lateral distance from the axis of the outer body; and fastener means for fastening the flange to one of the vertebral bodies.

8. A vertebral prosthesis for positioning between vertebral bodies, comprising in combination:

a tubular outer body having a platform on one end, a longitudinal axis and an axial fore;

an inner body having a cylindrical portion carried in the bore of the outer body for sliding telescoping movement along the axis of the outer body, the inner body having a platform on one end that is located exterior of the outer body;

securing means on each of the platforms for securing the platforms to adjacent vertebral bodies;

port means for introducing a liquid into the bore of the outer body to cause the inner body to move axially relative to the outer body to provide a desired length for the prosthesis between platforms;

check valve means located within one of the bodies for allowing liquid to be introduced into the outer body, but preventing the liquid from flowing out of the outer body; and wherein each of the securing means comprises:

a plurality of pins, each protruding in an axial direction from one of the platforms for anchoring in holes in one of the vertebral bodies;

a bracket having a base and a flange which extends from one side of the bracket transverse to the base;

means for mounting the base of the bracket to one of the platforms for sliding movement transverse to the axis of the outer body to position the flange at a selected lateral distance from the axis of the outer body; and fastener means for fastening the flange to one of the vertebral bodies.

9. A vertebral prosthesis for positioning between vertebral bodies, comprising in combination:

a tubular outer body having a platform on one end, a longitudinal axis and an axial bore;

an inner body having a cylindrical portion carried in the bore of the outer body for sliding telescoping movement along the axis of the outer body, the inner body having a platform on one end that is located exterior of the outer body;

securing means on each of the platforms for securing the platforms to adjacent vertebral bodies;

port means for introducing a liquid into the bore of the outer body to cause the inner body to move axially relative to the outer body to provide a desired length for the prosthesis between platforms;

check valve means located within one of the bodies for allowing liquid to be introduced into the outer body, but preventing the liquid from flowing out of the outer body; and wherein each of the securing means comprises:

a plurality of pins, each having a sharp tip, each protruding in an axial direction from one of the platforms for piercing and anchoring in soft portions of the vertebral bodies;

a bracket having a base and a flange which extends from one side of the bracket transverse to the base;

means for mounting the base of the bracket to one of the platforms for sliding movement transverse to the axis of the outer body to position the flange at a selected lateral distance from the axis of the outer body; and fastener means for fastening the flange to one of the vertebral bodies.

10. A vertebral prosthesis for positioning between vertebral bodies, comprising in combination:

a tubular outer body having a platform on one end, a longitudinal axis and an axial bore;

a tubular inner body having a cylindrical portion carried in the bore of the outer body for sliding telescoping movement along the axis of the outer body, the inner body having a platform on one end that is located exterior of the outer body;

a piston carried in the outer body for axial movement relative to the outer body;

a pin mounted to the piston, the pin having a sharp tip which protrudes through a hole provided in one of the platforms; and port means for introducing a liquid into the bore of the outer body to move the piston to cause the pin to pierce and anchor within one of the vertebral bodies and to cause the inner body to move axially relative to the outer body to provide a desired length for the prosthesis between platforms.

11. The prosthesis according to claim 10 further comprising:

a bracket having a base and a flange which extends from one side of the bracket transverse to the base;

means for mounting the base of the bracket to one of the platforms for sliding movement transverse to the axis of the outer body to position the flange at a selected lateral distance from the axis of the outer body; and fastener means for fastening the flange to one of the vertebral bodies.

* * * * *